United States Patent [19]

Hastings et al.

[11] Patent Number: 5,546,813
[45] Date of Patent: Aug. 20, 1996

[54] APPARATUS FOR DETERMINING FLUID FLOW

[75] Inventors: Calvin R. Hastings; Ernest M. Hauser, both of Pittsburgh; Robert C. Miller, New Alexandria, all of Pa.

[73] Assignee: Caldon, Inc., Pittsburgh, Pa.

[21] Appl. No.: 415,090

[22] Filed: Mar. 31, 1995

Related U.S. Application Data

[63] Continuation of Ser. No. 957,411, Oct. 6, 1992, abandoned.

[51] Int. Cl.$^6$ ............................................ G01F 1/00
[52] U.S. Cl. ............................................ 73/861.29
[58] Field of Search ........................... 73/861.18, 861.27, 73/861.28, 861.29, 861.31

[56] References Cited

U.S. PATENT DOCUMENTS

| | | | |
|---|---|---|---|
| 2,874,568 | 2/1959 | Petermann | 73/862.29 |
| 3,653,259 | 4/1972 | McShane | 73/861.27 |
| 4,078,427 | 3/1978 | Yoshida et al. | 73/861.28 |
| 4,094,193 | 6/1978 | Gerlach | 73/861.27 |
| 4,331,025 | 5/1982 | Ord, Jr. | 73/861.28 |
| 4,397,194 | 8/1983 | Soltz | 73/861.28 |
| 4,483,202 | 11/1984 | Ogura et al. | 73/861.27 |
| 4,633,719 | 1/1987 | Vander Heyden | 73/862.28 |
| 4,646,575 | 3/1987 | O'Hair et al. | 73/861.31 |
| 4,748,857 | 6/1988 | Nakagawa | 73/861.28 |
| 4,930,358 | 6/1990 | Motegi et al. | 73/861.28 |
| 5,115,670 | 5/1992 | Shen | 73/861.29 |

FOREIGN PATENT DOCUMENTS

| | | |
|---|---|---|
| 58-171624 | 10/1983 | Japan . |
| 58-171625 | 10/1983 | Japan . |
| 60-40916 | 3/1985 | Japan . |
| 60-202310 | 10/1985 | Japan . |
| 62-9223 | 10/1987 | Japan . |
| 62-9224 | 10/1987 | Japan . |
| 1-105857 | 7/1989 | Japan . |
| 0008516 | 11/1988 | WIPO ............................. 73/861.28 |

Primary Examiner—Richard Chilcot
Assistant Examiner—Ronald Biegel
Attorney, Agent, or Firm—Ansel M. Schwartz

[57] ABSTRACT

The present invention is an apparatus for determining the flow rate of a fluid in a pipe. The apparatus includes a device for providing acoustic energy on a diagonal path through the fluid. The diagonal providing device is in contact with the pipe. The apparatus also includes a device for providing acoustic energy on a diametrical path through the fluid. The diametrical providing device is in contact with the pipe. The apparatus is also comprised of a device for determining the flow of fluid in the pipe based on the acoustic energy of the diagonal providing device with the energy received by the diameterical receiving means used to determine the speed of sound of the fluid so the flow rate of fluid can be determined and the acoustic energy of the diametrical providing device. In one embodiment, the diagonal providing device is fixedly disposed on the pipe. In another embodiment, the diametrical providing device provides acoustic energy emitted in both directions on the diametrical path. The diagonal providing device preferably includes a first transducer and a second transducer located at diametrically opposed positions about the pipe. The first transducer and second transducer are preferably adapted to alternatively function as transmitter and receiver so as to cause ultrasonic signals to travel through the fluid along the diametric path. The diametrical providing device preferably includes a third transducer and a fourth transducer located at diagonally opposed upstream and downstream positions relative to one another.

21 Claims, 8 Drawing Sheets

APPARATUS FOR DETERMINING FLUID FLOW

This is a continuation of application Ser. No. 07/957,411 filed on Oct. 6, 1992, now abandoned.

FIELD OF THE INVENTION

The present invention relates in general to flowmeters. More specifically, the present invention is related to flowmeters using ultrasonic transducers for the noninvasive measurement of attributes of a fluid, such as its flow, in a pipe.

BACKGROUND OF THE INVENTION

A convenient and commonly used means of measuring fluid flow is by the use of ultrasonic flowmeters. This is typically accomplished by a system in which two transducers, located at angularly opposed upstream and downstream positions relative to one another are adapted to alternatively function as a transmitter and a receiver thereby causing ultrasonic signals to travel alternatively in upstream and downstream directions between the transducers. The difference in transit times between the upstream signal and the downstream signal can be used to calculate the flow rate of the fluid.

The present invention in a preferred embodiment provides a second set of transducers which are disposed in a diametrical opposed relation. These "cross path" transducers provide more information about the flow field, allowing for improvement in flow measurement accuracy and understanding of the flow field.

SUMMARY OF THE INVENTION

The present invention is an apparatus for determining the flow rate of a fluid in a pipe. The apparatus includes means for providing acoustic energy on a diagonal path through the fluid. The diagonal providing means is in contact with the pipe. The apparatus also includes means for providing acoustic energy on a diametrical path through the fluid. The diametrical providing means is in contact with the pipe. The apparatus is also comprised of means for determining the flow of fluid in the pipe based on the acoustic energy of the diagonal providing means and the acoustic energy of the diametrical providing means with the energy received by the diametrical receiving means used to determine the speed of sound of the fluid so the flow rate of fluid can be determined.

In one embodiment, the diagonal providing means is fixedly disposed on the pipe. In another embodiment, the diametrical providing means provides acoustic energy emitted in both directions on the diametrical path. The diametrical providing means preferably includes a first transducer and a second transducer located at diametrically opposed positions about the pipe. The first transducer and second transducer are preferably adapted to alternatively function as transmitter and receiver so as to cause ultrasonic signals to travel through the fluid alternatively along the diametric path.

The diagonal providing means preferably includes a third transducer and a fourth transducer located at diagonally opposed upstream and downstream positions relative to one another. The third transducer and the forth transducer are preferably adapted to alternatively function as a transmitter and receiver so as to cause ultrasonic signals to travel through the fluid in upstream and downstream directions along the diagonal path between the third transducer and the fourth transducer. The diametric path is adjacent to the diagonal path so that the transducers are sampling the same portion of fluid.

The determining means preferably comprises signal processing means for determining the flow of fluid in the pipe based on the transmission speed of ultrasonic signals transmitted between the first and second transducers and the third and fourth transducers.

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

Figure 1:
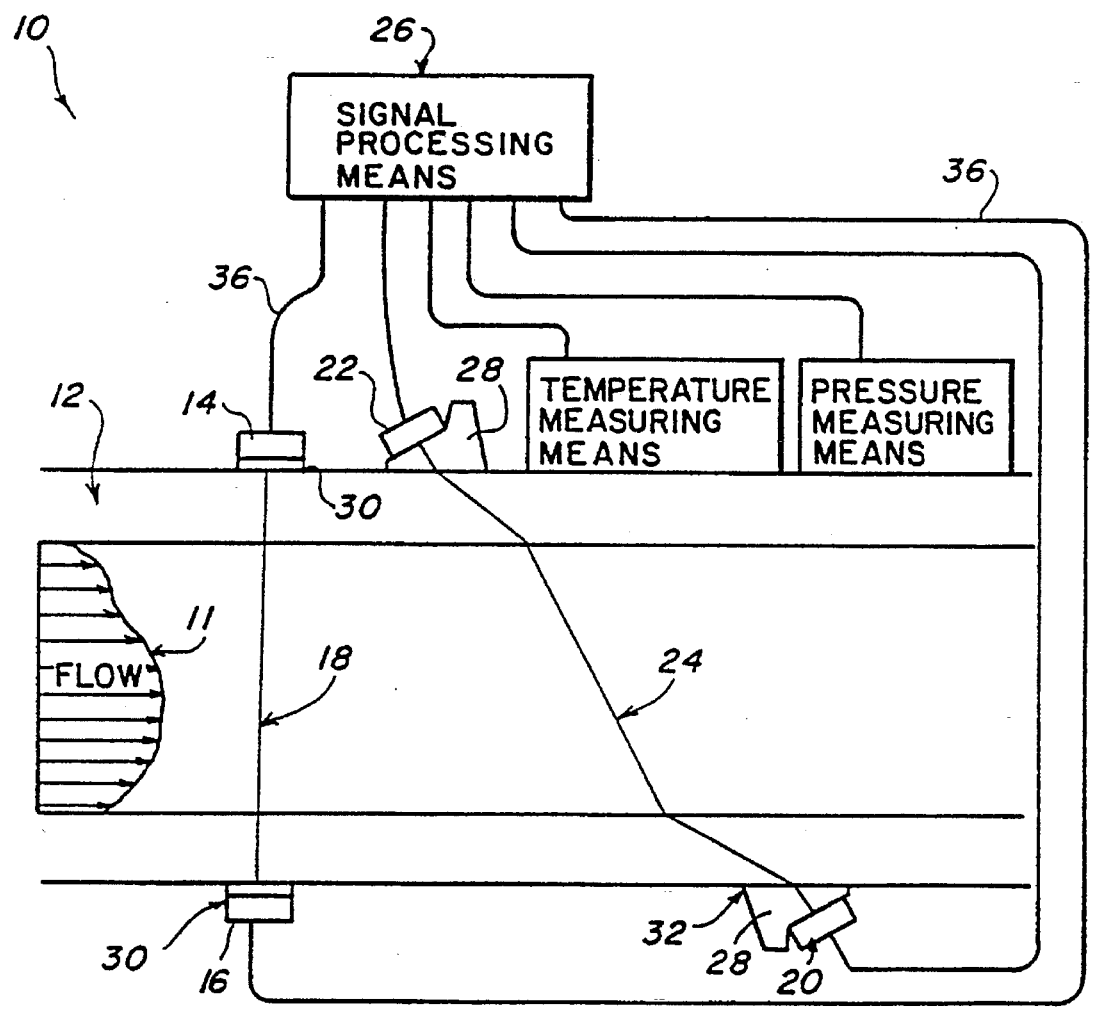
FIG. 1 is a schematic representation showing an apparatus for determining fluid flow in a pipe.
Figure 2:
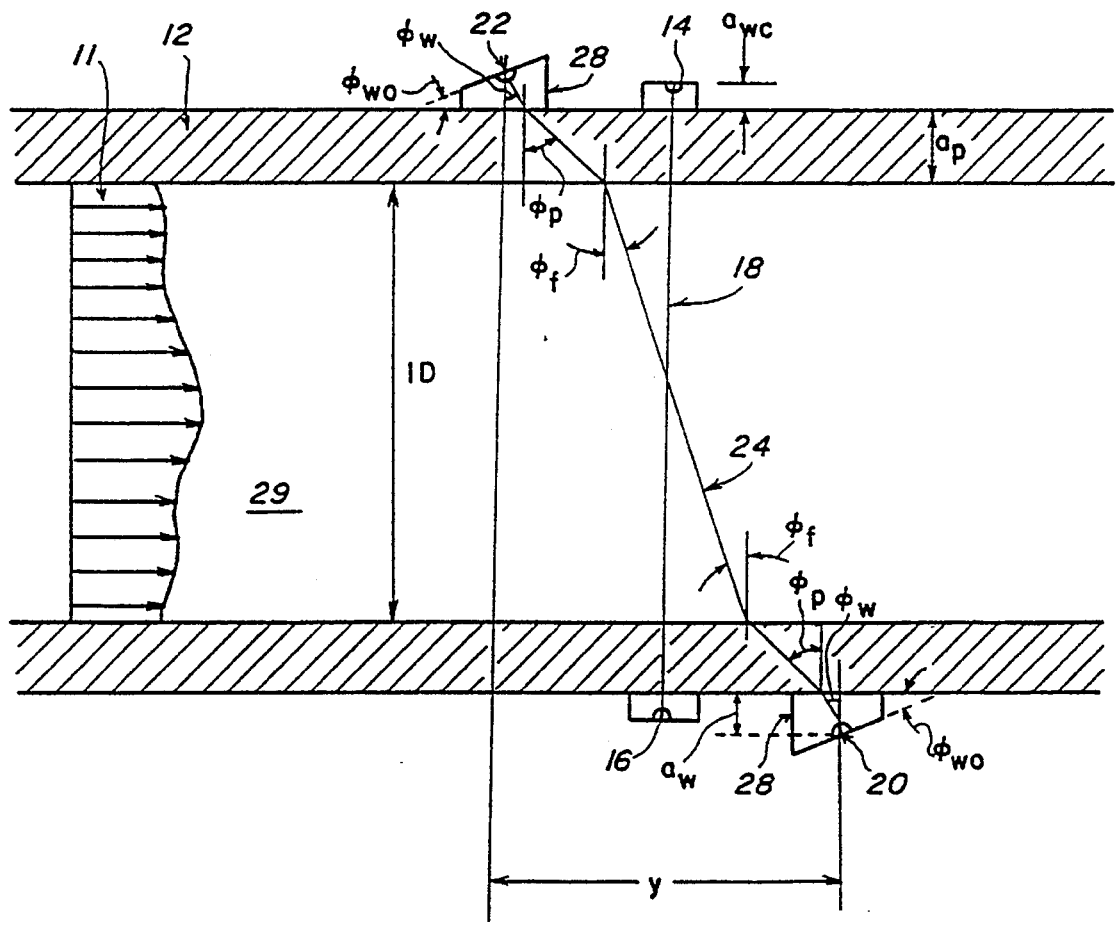
FIG. 2 is a schematic representation showing the geometric parameters associated with the apparatus for determining fluid flow in a pipe.

Referring now to the drawings wherein like reference numerals refer to similar or identical parts throughout the several views, and more specifically to FIGS. 1 and 2 thereof, there is shown an apparatus 10 for determining the flow rate of a fluid 11 in a pipe 12. The apparatus 10 comprises means for providing acoustic energy on a diagonal path 18 through the fluid 11. The diagonal providing means is in acoustic contact with and preferably disposed on the pipe 12. The apparatus 10 also comprises means for providing acoustic energy on a diametrical path 24 through the fluid 11. The diametrical providing means is in acoustic contact with and preferably disposed on the pipe 12. The apparatus 10 is also comprised of means for determining the flow of fluid 11 in the pipe 12 based on the acoustic energy of the diagonal providing means and the acoustic energy of the diametrical providing means. In one embodiment, the diagonal providing means is fixedly disposed on the pipe 12. In another embodiment, the diametrical providing means provides acoustic energy emitted in both directions on the diametrical path 24.

Referring to FIG. 1, the diametrical providing means is preferably comprised of a first transducer 14 and a second transducer 16 located at diametrically opposed upstream and downstream positions relative to one another. The first transducer 14 and second transducer 16 are preferably adapted to alternatively function as transmitter and receiver so as to cause ultrasonic signals to travel through the fluid 11 alternatively in upstream and downstream directions along a diametric path 18 between the first transducer 14 and the second transducer 16.

The diagonal providing means is preferably a third transducer 20 and a fourth transducer 22 located at diagonally opposed positions about the pipe 12. The third transducer 20 and the forth transducer 22 are preferably adapted to alternatively function as a transmitter and receiver so as to cause ultrasonic signals to travel through the fluid 11 along a diagonal path 24. The diametric path 18 is adjacent to the diagonal path 24 so that the transducers are essentially sampling the same portion of fluid 11.

The determining means preferably comprises signal processing means 26 for determining the flow of fluid 11 in the pipe 12 based on the transmission speed of ultrasonic signals transmitted between the first and second transducers 14, 16 and the third and fourth transducers 20, 22, respectively.

Preferably, the transducers 14, 16, 20 and 22 are mounted on the outside of the pipe 12 and thus do not disturb the fluid flow therein. The coupling between the third and fourth transducers 20, 22 and the pipe 12 is preferably accomplished by mounting the third and fourth transducers 20, 22 onto a coupling wedge 28 which can be comprised of vespal or lucite, for example. The first and second transducers 14, 16 are mounted on a pad 30, which can also be comprised of vespal or lucite. The coupling between the wedges 28 and pads 30 and the pipe 12 can be enhanced by providing a layer 32, such as silicon rubber. The layer 32 helps in preventing disruption or dispersion of the ultrasonic signals as they travel from their respective wedge 28 or pad 30 to the pipe 12. Preferably, the signal processing means 26 includes means for measuring the transit time of ultrasonic signals transmitted between the first and second transducers 14, 16 and the transit time between ultrasonic signal transmitted between the third and fourth transducers 20, 22, respectively.

Figure 4:
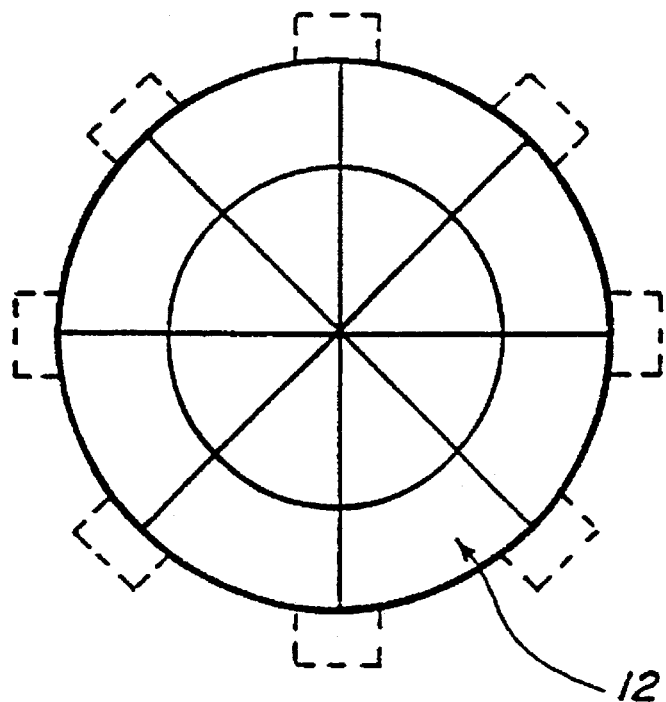
FIG. 4 is a schematic representation of the apparatus for determining fluid flow in a pipe having a four ultrasound paths.

In a preferred embodiment, there is a plurality of diagonal sets of transducers for transmitting ultrasonic signals through the fluid 11 along a plurality of diagonal paths 24 and an equal number of diametrical sets of transducers for transmitting ultrasonic signal through the fluid 11 along a plurality of diametrical paths 18. FIG. 4 shows a cross section through the axis of the pipe 12 showing a four path system. Since FIG. 4 is a cross sectional view, the transducers shown can be either diagonal sets or diametrical sets. Likewise, the four paths shown can be either diagonal paths 18 or diametrical paths 24.

It should be noted that in FIG. 2 and the specification, the following nomenclature is used:

Q=total flow in pipe 12 (cubic inches/sec)
Π=Pi=3.141593
ID=Inside diameter of pipe 12 (inches)
PF=Hydraulic profile factor=ratio of average velocity over whole pipe 12 to average velocity along diameter
$c_f$=velocity of sound in fluid 11 (inches/sec)
$\phi_f$=angle of acoustic path in fluid 11
$t_{d1}$=transit time along diagonal path 18 from transducer 14 to transducer 16
$t_{d2}$=transit time along diagonal path 18 from transducer 16 to transducer 14
$\Delta t_d$=difference in time along diagonal path 18 (seconds) that is $\Delta t_d = t_{d1} - t_{d2}$
$t_{c1}$ is transit from transducer 20 to transducer 22
$t_{c2}$ is transit from cross path transducer 22 to transducer 20
$\Delta t_c$=difference in time along diametrical cross path 24 (seconds) that is $\Delta t_c = t_{c1} - t_{c2}$
$c_w$=velocity of sound in transducer wedge 28 and pad 30 (inches/sec)
$\phi$=mechanical wedge 28 angle
$a_w$=height of wedge (inches)
$a_{wc}$=height of pad 30
$a_p$=wall thickness of pipe 12 (inches)
$\phi_p$=acoustic path angle in pipe 12
$\phi_w$=acoustic path angle in wedge 28
$c_{pt}$=velocity of transverse wave in pipe 12 (inches/sec)
$c_{pl}$=velocity of longitudinal wave in pipe 12 (inches/sec)
$t_d$=average transit time along diagonal path 18 (seconds) that is $t_d = (t_{d1} + t_{d2})/2$
$t_c$=average transit time along diametrical path 18 (seconds) that is $t_c = (t_{c1} = t_{c2})/2$
y is the distance between centers of transducers 14, 16
$y_o$ is the calculated value of y to be used in initial set up
temp=Temperature in degrees F
press=Pressure in psi absolute
press=pressure gauge+14.7
tr, vt, dvdp, tc are parameters used in the calculation of velocity of sound in water
Acpl, Bcpl, Acpt, Bcpt are constants used in calculation of velocity of sound in pipe (dependent on pipe material)
Acw, Bcw, Ccw are constants used in calculation of velocity of sound in wedge (dependent on wedge material)

The flow rate Q of the fluid is calculated by:

$$Q = (\pi \cdot ID^2 \cdot PF/4) \cdot v_a$$

since, $$v_a = v_d/\sin\phi_f - v_c/\tan\phi_f$$

and, $$v_d = (c_f^2 \cdot \cos\phi_f/2 \cdot ID) \cdot (\Delta t_d)$$

$$v_c = (c_f^2/2 \cdot ID) \cdot (\Delta t_c) \quad (0)$$

Thus, $$v_a = (c_f^2/2 \cdot ID \cdot \tan\phi_f) \cdot (\Delta t_d - \Delta t_c)$$

substituting into the original equation, $$Q = (\pi \cdot ID \cdot PF \cdot C_f^2/8 \cdot \tan\phi_f) \cdot (\Delta t_d - \Delta t_c) \quad (1)$$

For acoustic path-to-transmitter length ratios less than 16:1, $\phi_f$ is calculated using Snells law relationship as follows:

$$\phi_f = \sin^{-1}(c_f \sin\phi_w/c_w)$$

For acoustic path-to-transmitter length ratios greater than 100:1, calculation of $\phi_f$ is given by solution of the following simultaneous equations:

$$t_d = 2 \cdot a_w/\cos\phi_w \cdot c_w + 2 \cdot a_p/\cos\phi_p \cdot c_{pt} + ID/\cos\phi_f \cdot c_f \quad (2)$$

$$\sin\phi_f/c_f = \sin\phi_p/c_{pt} \text{ (Snells law)} \quad (3)$$

$$\sin\phi_f/c_f = \sin\phi_w/c_w \text{ (Snells law)} \quad (4)$$

Ideally, the acoustic path-to-transmitter length ratio should be chosen to fall clearly into one of these regions. Alternatively, if this cannot be achieved, then the fourth transducer is moved axially along the pipe 12 until the position is found at which the signal transferred from the third transducer 20 to the fourth transducer 22 is a maximum. At this point, either set of the above equations can be used.

If y is known $\phi_f$ is given by solution of the following set of equations:

$$y = 2 \cdot a_w \cdot \mathrm{Tan}\phi_w + 2 \cdot a_p \cdot \mathrm{Tan}\phi_p + ID \cdot \mathrm{Tan}\phi_f$$

$$\mathrm{Sin}\phi_f/c_f = \mathrm{Sin}\phi_p/c_{pt} \text{ Snells law}$$

and $$\mathrm{Sin}\phi_f/c_f = \mathrm{Sin}\phi_w/c_w \text{ Snells law}$$

Calculation of $y_o$ $$\mathrm{Sin}\phi_f = c_f \cdot \mathrm{Sin}\phi_{wo}/c_w \text{ Snells law}$$

$$\mathrm{Sin}\phi_p = c_{pt} \cdot \mathrm{Sin}\phi_{wo}/c_w \text{ Snells law}$$

$$y_o = 2 \cdot a_w \cdot \mathrm{Tan}\phi_w + 2 \cdot a_p \cdot \mathrm{Tan}\phi_p + ID \cdot \mathrm{Tan}\phi_f$$

Calculation of $c_f$ is given by solution of equation:

$$t_c = ID/c_f + 2 \cdot a_p/c_{pt} + 2 \cdot a_{wc}/c_w \qquad (5)$$

The speed of sound values are dependent on temperature. $t_c$ is measured with the first transducer 14 and the second transducer 16 through the diametric path 18 therebetween. $C_{pt}$, $C_{pl}$ and $C_w$ are determined by the following equations.

$$c_{pt} = Acpt*(1 + Bcpt*\mathrm{temp}) \qquad (6)$$

$$c_{pl} = Acpl*(1 + Bcpl*\mathrm{temp}) \qquad (7)$$

$$c_w = Acw*(1 + Bcw*\mathrm{temp} + Ccw*\mathrm{temp}^2) \qquad (8)$$

ID, $a_p$ and $a_{wc}$ are known (measured) from the specific application of the apparatus.

With $c_f$ known by solution of Equation (5), $t_d$ measured with the third transducer 20 and the fourth transducer 22 through the diagonal path 24 therebetween, and $a_w$, $c_w$ and $a_p$, $c_{pt}$ and ID known, solution of, for example, the three Equations (2)–(4) determine the three unknowns $\phi_w$, $\phi_p$ and $\phi_f$ in these equations. Consequently, Q can then be determined since every variable in Equation (1) is now known. For instance, for carbon steel pipe 12
Acpl=2356000
Bcpl=0.0000735
Acpt=127700
Bcpt=0.0000925
For vespal wedges 28
Acw=98299
Bcw=0.0003960
Ccw=2.08E-7
To calculate $c_f$ in water temperatures>200° F.

$$tr = \mathrm{temp} - 175.1 \qquad (9)$$

$$vt = 5290.52 - 0.15302*tr - 0.0138265*tr^2 + 3.326E-6 \ *tr^3 + 3.11042*tr^4 - 5.1131E-11*tr^5 \qquad (10)$$

$$dvdp = 756.78/(725 - \mathrm{temp}) + 6.3846 - 0.034241*(725 - \mathrm{temp}) + 7.4075 - 5*(725 - \mathrm{temp})^2 - 5.666E-8*(725 - \mathrm{temp})^3 \qquad (11)$$

$$vtp = vt - (4437 - \mathrm{press})*dvdp*0.02253 \qquad (12)$$

$$c_f = vtp*12 \qquad (13)$$

To calculate $c_f$ at water temperatures<200° F.

$$tc = (\mathrm{temp} - 32)/1.8 \qquad (14)$$

-continued $$c_f = 100/2.54* (1402.49 + 5.0511*tc - .05693*tc^2 + 2.7633E - 4*tc^3 - \&.1558E - 7tc^4)$$

The above equations assume that the wedges 28, pipe 12 and fluid 11 are all at the same temperature. When the temperature of the fluid 11 is different from that of ambient temperature, it is desirable to provide insulation or other means to insure that the temperature is uniform or to modify the equations given above to correct for these differences. For small gradients it is sufficient to assign different temperatures to the wedges and pipe thus temp(pipe)=temp(fluid)−$\Delta t_p$
temp(wedge)=temp(fluid)−$\Delta t_w$
temp(cross wedge)=temp(fluid)−$\Delta t_{wc}$ where
$\Delta t_w$ is the difference between the fluid temperature and the average temperature of the wedge
$\Delta t_{wc}$ is the difference between the fluid temperature and the average temperature of the cross wedge or pad
$\Delta t_p$ is the difference between the fluid temperature and the average temperature of the pipe
For large gradients, it is desirable to have detailed knowledge of the temperature distribution in the pipe and wedge and to use ray tracing techniques as practiced in the design of optical instruments to calculate the times spent in the wedge and pipe and contribution of the pipe and wedge to the y displacement.

If the temperature of the fluid is not known, as shown in the "REM Calculation of Fluid Temperature" section of the program of the Appendix, $c_f$ as well as the temperature of the water can be arrived at in an iterative loop technique that essentially picks a temperature value of the water based on the known temperature limits of the water, uses this temperature value to arrive at values of $c_f$ $c_{wc}$ and $c_{pt}$, and then uses the values of $c_f$, $c_{wc}$ and $c_{pt}$ in equation (5) to arrive at a calculated value of $t_c$. The actual measured value of $t_c$ is then compared with the calculated value of $t_c$.

If the calculated value of $t_c$ does not match the measured value of $t_c$, different temperature values are sequentially picked in the program and the loop is reiterated until the calculated value of $t_c$ matches the measured value of $t_c$. The picked temperature and the calculated value of $c_f$ during the last loop are then known to be the actual values of temperature and $c_f$.

In this manner, both the speed of sound in the fluid, $c_f$, and the temperature of the fluid 11 flowing in the pipe 12 can be determined by mounting a pair of ultrasonic transducers in a diametrical opposed relation on the pipe 12 and using signal processing means to determine a measured value of $t_c$.

In the operation of the invention, the transducers 14, 16, 20 and 22 are preferably strap-on types. The strap-on transducer assembly contains a piezoelectric transducer, a coupling wedge 28 or pad 30 and a protective cover. The transducer converts the electrical energy to ultrasonic energy which the wedge 28 and pads 30 directs into the pipe 12 at the proper angle. The protective cover provides a fitting for the transducer cable 36 conduit as well as protection of the transducer.

After precisely locating the transducer on the surface of the pipe 12, the transducer wedge is coupled acoustically to the pipe wall and then secured with strapping material, magnetic holders, or welded brackets.

The transducer signal cable is a twinax twisted pair with a shield with an appropriate jacket for underwater or above ground use as required. It is connected to the transducer at one end and to the signal processing means 26 at the other, normally without splices.

Figure 3:
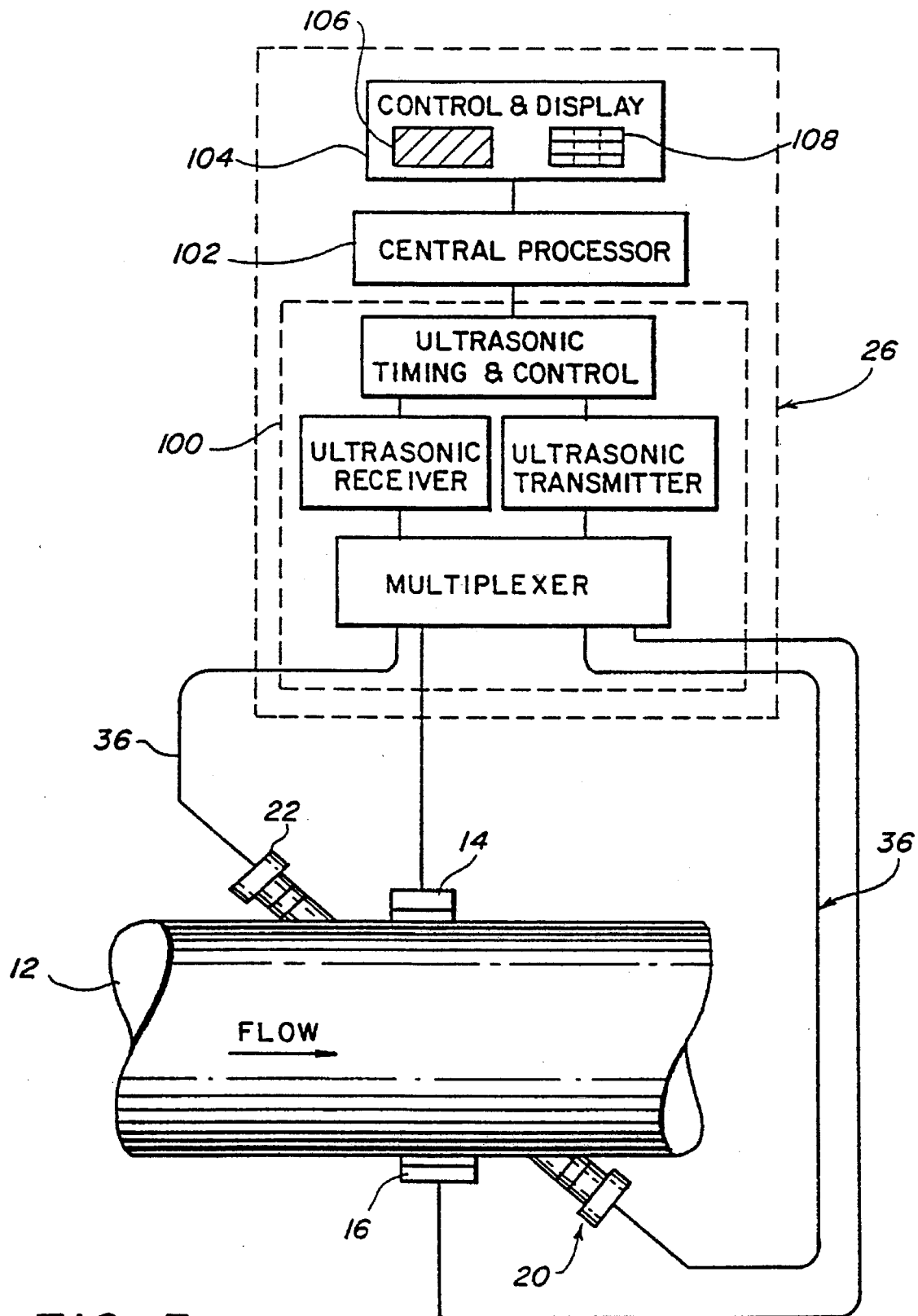
FIG. 3 is a schematic representation showing the signal processing means of the apparatus for determining fluid flow in a pipe.

The signal processing means 26 is comprised of three major functional units. These are the Acoustic Processing Unit 100 (APU), the Central Processing Unit 102 (CPU), and the Control and Display Panel 104 (CDP). FIG. 3 provides a functional diagram of these electronics.

The APU 100 controls the transmission and reception of ultrasonic signals to and from the transducers. Electronic pulses are generated and sent to the transducers, where the energy is converted into ultrasound and directed upstream or downstream in directly into the pipe depending on which transducer is transmitting, converted back into electronic pulses, and received. Transmit times of pulses are measured with a 100 Mhz clock, alternately upstream and downstream, every 4 ms to assure that data is essentially simultaneous for upstream and downstream transit times. These time measurements are stored and then sent to the central processing unit 102 for mathematical manipulation.

The APU 100 typically is equipped with two transmitter/receiver boards which control a total of four ultrasonic diagonal paths 18. Additionally, there are two transmitter/receiver boards to control four ultrasonic diametric paths 24.

The CPU 102 consists of a 286 microprocessor and I/O with software suited specifically to the needs of the application. The CPU 102 provides a number of important functions, including processing the transit time measurements from the APU 100. Flow totalizers are also updated according to Euler's equation. At the same time as high speed calculations are being processed, the displays are updated, electronic checks are being made of the entire APU 100 circuitry, user keypad commands are followed, and outputs are updated.

The CDP 104 functions as the user interface. A full screen display 106 provides readouts of flowrates, flow totals, diagnostics, set-up parameters, and pertinent performance characteristics. A numeric keypad 108 allows the operator to select desired display screens without consulting a programmer's handbook and without need of attaching a separate computer.

Listed below in Tables 1 through 3 are summaries of the calculated parameters for two verification sites. These verification sites were the Alden Research Laboratories (ARL) and the Tennessee Valley Authority (TVA) Sequoyah Nuclear Power Plant. The ARL test used a 16 in OD pipe with fluid temperature at approximately 105° Fahrenheit. (The data presented below are documented by ARL which is an NIST approved facility). The TVA test used a 32 in OD pipe with fluid temperature at approximately 435° Fahrenheit. Independent error analysis determined its accuracy to be ±0.9% of measured flow.

TABLE 1

Flow Calculation at ARL 12/18/91

Conditions:

| | |
|---|---|
| ID | = 15.028 in (Direct Measurement) |
| pressure | = 50 psi |
| $a_p$ | = .495 in (Direct Measurement) |
| temp | = 105.32° (ARL Reference) |
| Q | = 18,390 gpm (ARL Reference) |
| $c_w$ | = 92,170 in/sec (Direct Measurement) |
| $\phi_{wo}$ | = 30.550 |
| $c_{pl}$ | = 233,774 in/sec (Curve fit from Published values) |

TABLE 1-continued

Flow Calculation at ARL 12/18/91

| | |
|---|---|
| $a_{wc}$ | = .25 in |
| $c_{pt}$ | = 125,454 in/sec (Curve fit from Published values) |
| $a_w$ | = .586 in |

LEFM Measured values:

| | |
|---|---|
| $t_{d1}$ | = 291.86 μsec |
| $t_{d2}$ | = 290.66 μsec |
| $t_{d1}$ | = 241.45 μsec |
| $t_{c2}$ | = 241.45 μsec |
| $\Delta t_d$ | = 1218 ns |
| $t_c$ | = 241.45 μsec |
| $\Delta t_c$ | = −4 ns |
| $t_d$ | = 291.26 μsec |

LEFM Calculated values:

| | |
|---|---|
| $c_f$ | = 60,260 in/sec |
| temp | = 105° |
| Q | = 18,488 gpm |
| $\phi_r$ | = 19.4° |
| $\phi_w$ | = 30.53° |
| $\phi_p$ | = 43.75° |
| y | = 6.92 in |
| $y_o$ (calculated) | = 6.92 in |

TABLE 2

Flow Calculation at ARL 12/18/91

Conditions:

| | |
|---|---|
| ID | = 15.028 in (Direct Measurement) |
| $a_p$ | = .495 in (Direct Measurement) |
| temp | = 105.19° (ARL Reference) |
| Q | = 13,430 gpm (ARL Reference) |
| $c_w$ | = 92,170 in/sec (Direct Measurement) |
| $c_{pl}$ | = 233,774 in/sec (Curve fit from Published values) |
| $c_{pt}$ | = 125,454 in/sec (Curve fit from Published values) |

LEFM Measured values:

| | |
|---|---|
| $t_d$ | = 291.26 μsec |
| $t_c$ | = 241.45 μsec |
| $\Delta t_d$ | = 890 ns |
| $\Delta t_c$ | = −3 ns |

LEFM Calculated values:

| | |
|---|---|
| $c_f$ | = 60,260 in/sec |
| temp | = 105° |
| Q | = 13,480 gpm |
| $\phi_r$ | = 19.4° |

TABLE 3

Flow Calculation at TVA Sequoyah 2/6/92

Conditions:

| | |
|---|---|
| ID | = 29.92 in (Indirect Measurement) |
| $a_p$ | = 1.194 in (Direct Measurement) |
| temp | = 428° (TVA RTD Measurement) |
| $c_w$ | = 82,750 in/sec (Direct Measurement and Curve Fit) |
| $c_{pl}$ | = 223,466 in/sec (Curve fit from Published values) |
| $c_{pt}$ | = 124,322 in/sec (Curve fit from Published values) |

LEFM Measured values:

| | |
|---|---|
| $t_d$ | = 670.32 μsec |
| $t_c$ | = 612.22 μsec |
| $\Delta t_d$ | = 1413 ns |

TABLE 3-continued

Flow Calculation at TVA Sequoyah 2/6/92

| $\Delta t_c$ | = 1 ns |
|---|---|
| LEFM Calculated values: | |
| $c_f$ | = 50,386 in/sec |
| temp | = 428.8° |
| Q | = 13.518 Mlbs/hr |
| $\phi_f$ | = 19.4° |

Figure 5:
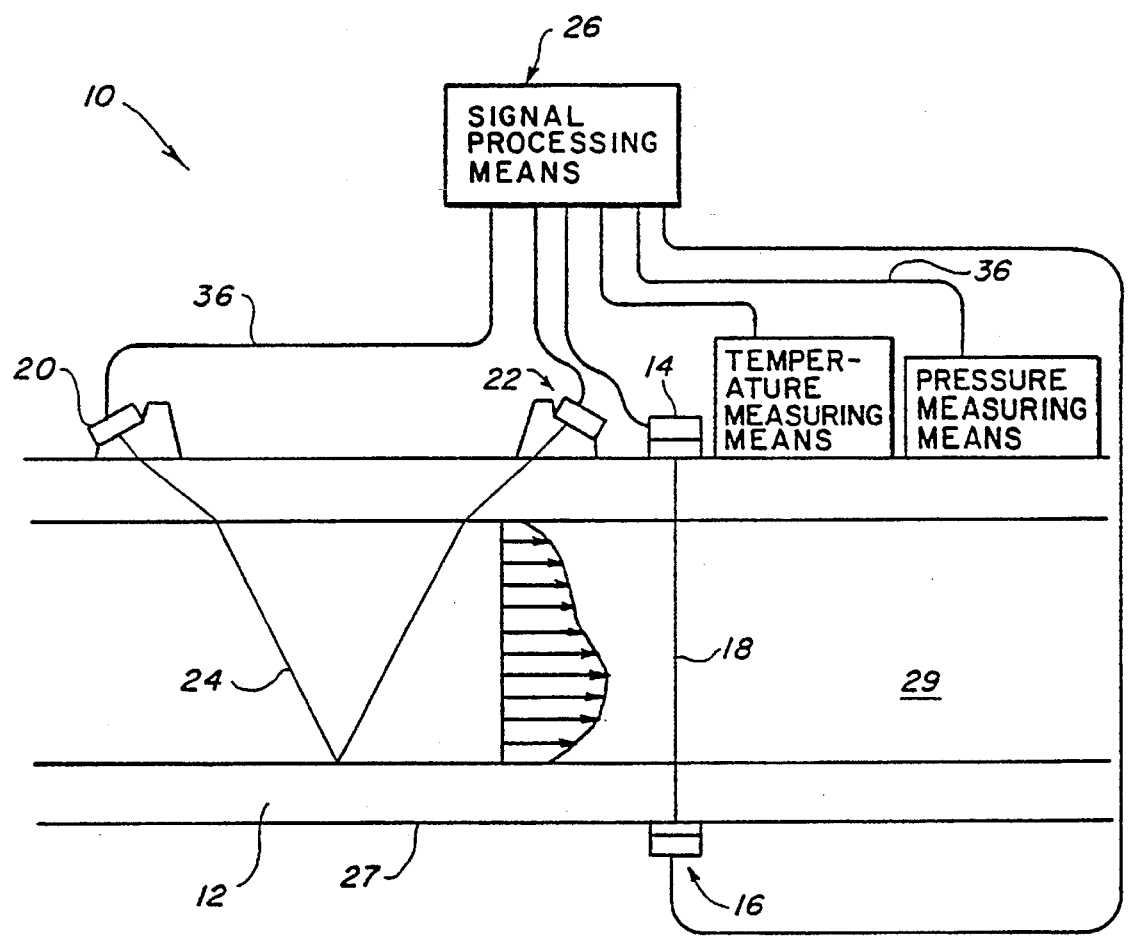
FIG. 5 is a schematic representation showing an apparatus for determining fluid flow in a pipe using a bounce path.

In an alternative embodiment, as shown in FIG. 5, the third transducer 20 and the fourth transducer 22 are aligned with each other such that acoustic energy transmitted by the third transducer 20 follows a diagonal path to the fourth transducer 22 which is formed by reflection of the acoustic energy off of the pipe 12. This configuration of the apparatus 10, as shown in FIG. 5, is otherwise known as the bounce path configuration. The first transducer 14 and the second transducer 16 which create the diametrical path 18, are disposed adjacent the diagonal path 24 that forms the bounce path, either between the third transducer 20 and fourth transducer 22 or outside the third transducer 20 or fourth transducer 22. The equations described above are also applicable to determine flow in the bounce path configuration of FIG. 5. An example of such a configuration is the following:

Q=472 gpm
ID=27.25 inches
PF=1.00
$c_f$=47,275.7 inches
$\phi_p$=18.35°
$t_{d1}$=385.180 μsec
$t_{d2}$=385.000 μsec
$\Delta t_d$=180 nsec
$t_{c1}$=179.008 μsec
$t_{c2}$=179.000 μsec
$\Delta t_c$=8 nsec
$c_w$=92,046.09 inches/sec
$\phi_{wo}$=38.52°
$a_w$=0.642 inches
$a_{wc}$=0.250 inches
$a_p$=0.360 inches
$\phi_p$=57.74°
$\phi_w$=37.80°
$c_{pl}$=126,989.7 inches/sec
$c_{pt}$=231,992.8
$t_d$=385.090 μsec
$t_c$=179.004 μsec
y=7.5
$y_o$=7.423
temp=74° F.
pressure=775 psi Conditions
Pipe ID=7.9529 inches
$a_p$=0.3605 inches
temp=74°
$c_{pl}$=231,945.8 in/sec (from tables)
$c_{pt}$=126,956.3 in/sec (from tables)
$c_w$=91,987.1 (direct measurement)

LEFM Measurements
$t_d$=386 μsec
$t_c$=180 μsec
$\Delta t_d$=177 nsec
$\Delta t_c$=8 nsec LEFM Calculated Values
$c_f$=47,001.3 in/sec. ($\phi_w$=37.18°)
Q=468 gpm ($\phi_p$=56.51°)
$\phi_f$=17.98°

Figure 6:
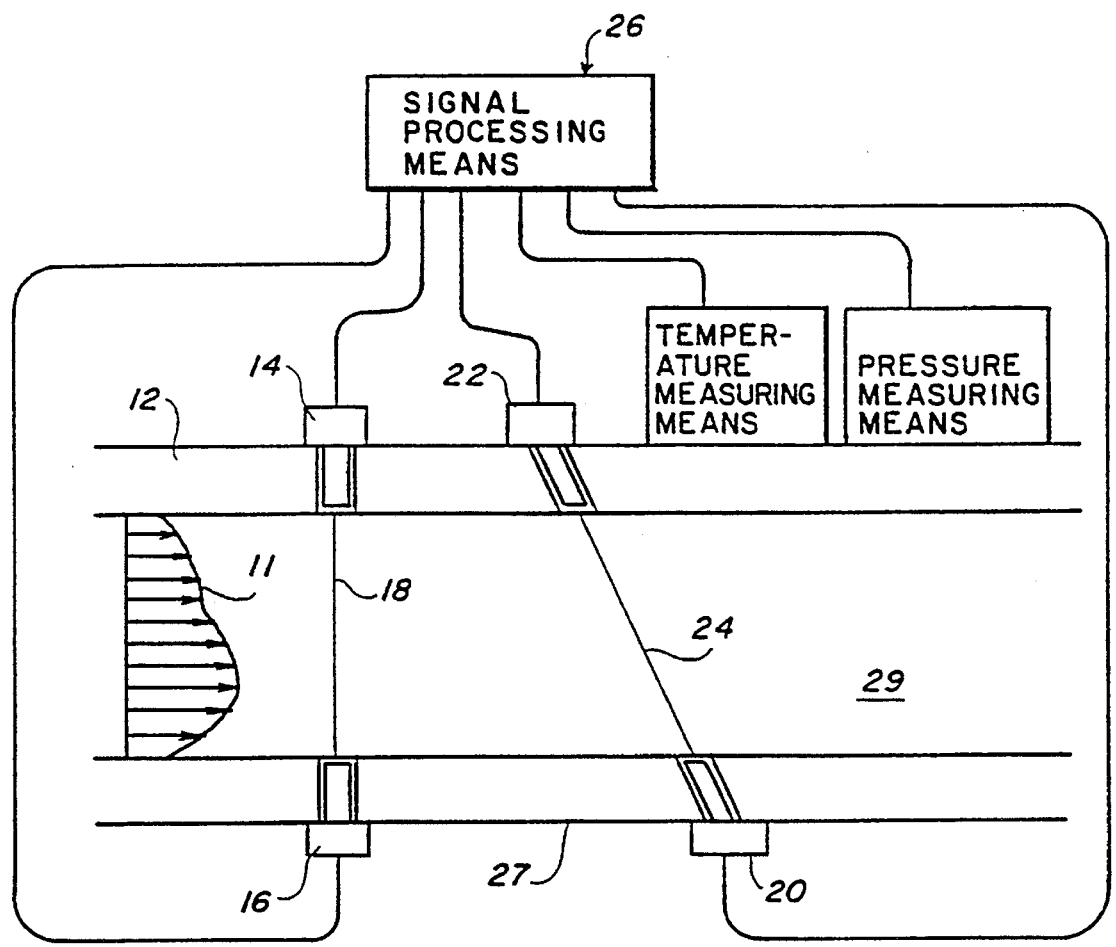
FIG. 6 is a schematic representation of an apparatus for determining fluid flow using transducers disposed below the pipe's surface.

In another alternative embodiment, as shown in FIG. 6, the pipe 12 has an outside surface 27 and an interior 29 and the first transducer 14 and second transducer 16 are disposed in the pipe 12 beneath the outside surface 27 such that acoustic energy transmitted by the first transducer 14 is introduced into the interior 29 of the pipe 12, an acoustic energy is received by the second transducer 16 directly from the interior 29 of the pipe 12 as shown in FIG. 6. The diametrical path 18 is thus formed without having acoustic energy, preferably ultrasonic energy, passing directly through the pipe 12. Preferably, the third transducer 20 and fourth transducer 22 are disposed in the pipe 12 beneath the outside surface 27 such that acoustic energy transmitted by the third transducer 20 is introduced directly into the interior 29 of the pipe, and acoustic energy is received by the fourth transducer 22 directly from the interior 29 of the pipe 12 after it has taken a diagonal path 24 therethrough. Of course, the third transducer 20 and fourth transducer 22 can be mounted on the outside 27 of the pipe 12 as described above, or, the various transducers can be mounted on or below the outside surface 27 depending on the design choice such that only one transducer, three transducers, etc. can be on or below the outside surface 27. The algorithm associated with calculation of the flow and other relevant factors for the embodiment shown in FIG. 6 can be found in Caldon technical report DS-112-991 (incorporated by reference) with respect to a single pair of transducers forming a diagonal ultrasonic path. For the pair of transducers forming the diametrical ultrasonic path θ=90°, Cos θ=1 yielding the transverse flow velocity V. For a 4-path configuration, see Caldon technical report DS-116-392 (incorporated by reference). The placement of the transducers beneath the outside surface 27 of the pipe 12 is well known. See Caldon technical report installation procedure SP1041 Rev. C, incorporated by reference.

The present invention also pertains to an apparatus for creating a transverse velocity profile of fluid flowing in a pipe 12. The apparatus comprises means for obtaining a transverse velocity of fluid in a plurality of different locations in the pipe 12 by introducing energy into the pipe 12 and analyzing the energy. Preferably, the obtaining means includes means for providing acoustic energy along a plurality of diametrical paths in the pipe 12, all of which are in a common cross section of the pipe 12, and producing an information signal corresponding to the transverse velocity of the plurality of different locations. The providing means can be a plurality of transducers which create a plurality of diametrical paths 18 in the pipe 12 as shown in FIG. 4. Each diametrical path 18 identifies the transverse velocity component associated with a corresponding location in the pipe 12. The transverse velocity corresponding to each diametrical path 18 can be determined by Equation (0).

The apparatus is also comprised of means for forming a transverse velocity profile from the transverse velocities at the plurality of different locations. The forming means is in communication with the obtaining means. Preferably, the forming means includes signal processing means 26. The signal processing means 26 receives the information signal and determines the transverse velocity associated with each location. Each pair of transducers which form a diametrical path 18 can be connected to signal processing means 26 as described above to calculate the transverse velocity for the corresponding diametrical path 18. Preferably, the more diametrical paths 18 in a given cross section of the pipe, the more accurate the transverse velocity flow profile will be.

Figure 9:
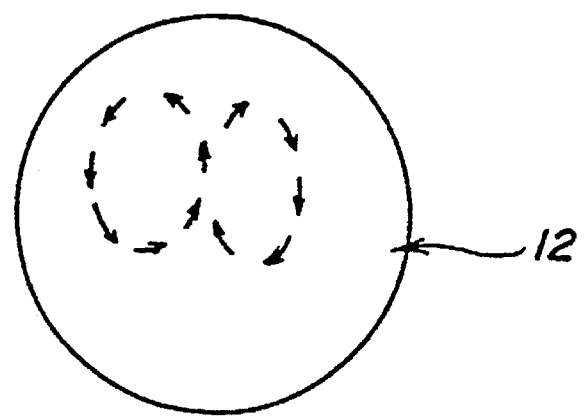
FIG. 9 is an image of a transverse velocity profile of a pipe.

Preferably, the forming means includes a monitor in which the transverse velocity of the locations are displayed together to show the transverse velocity profile. An example of a display that would appear on a monitor is shown in FIG. 9 which shows the rotational component both in the clockwise and counterclockwise direction cross section of the pipe 12. A ratio of $V_c:V_D$ can be used to deduce the flow profile characteristic (see Weske, J. "Experimental Investigation of Velocity Distributions Downstream of Single Duct Bends," NACA-TN-1471, January, 1948, incorporated by reference). The flow profile characteristic can be used to choose path(s) with the lowest diametrical to diagonal velocity ratio.

The present invention also pertains to an apparatus for determining transverse velocity of fluid in a pipe 12. The apparatus is comprised of means for actively testing the flowing fluid with energy and producing a test signal corresponding to the transverse velocity of the fluid. The testing means is in contact with the pipe 12. The apparatus 106 is also comprised of signal processing means 26 for determining the transverse velocity of the fluid based on the test signal. The signal processing means 26 is in communication with the transverse velocity testing means 106. As described above, the testing means is preferably a first transducer 14 and a second transducer 16 which are in contact with the pipe 12 such that they form a diametrical path 18. From Equation (0), the transverse velocity can be obtained with the signal processing means 108.

Figure 7:
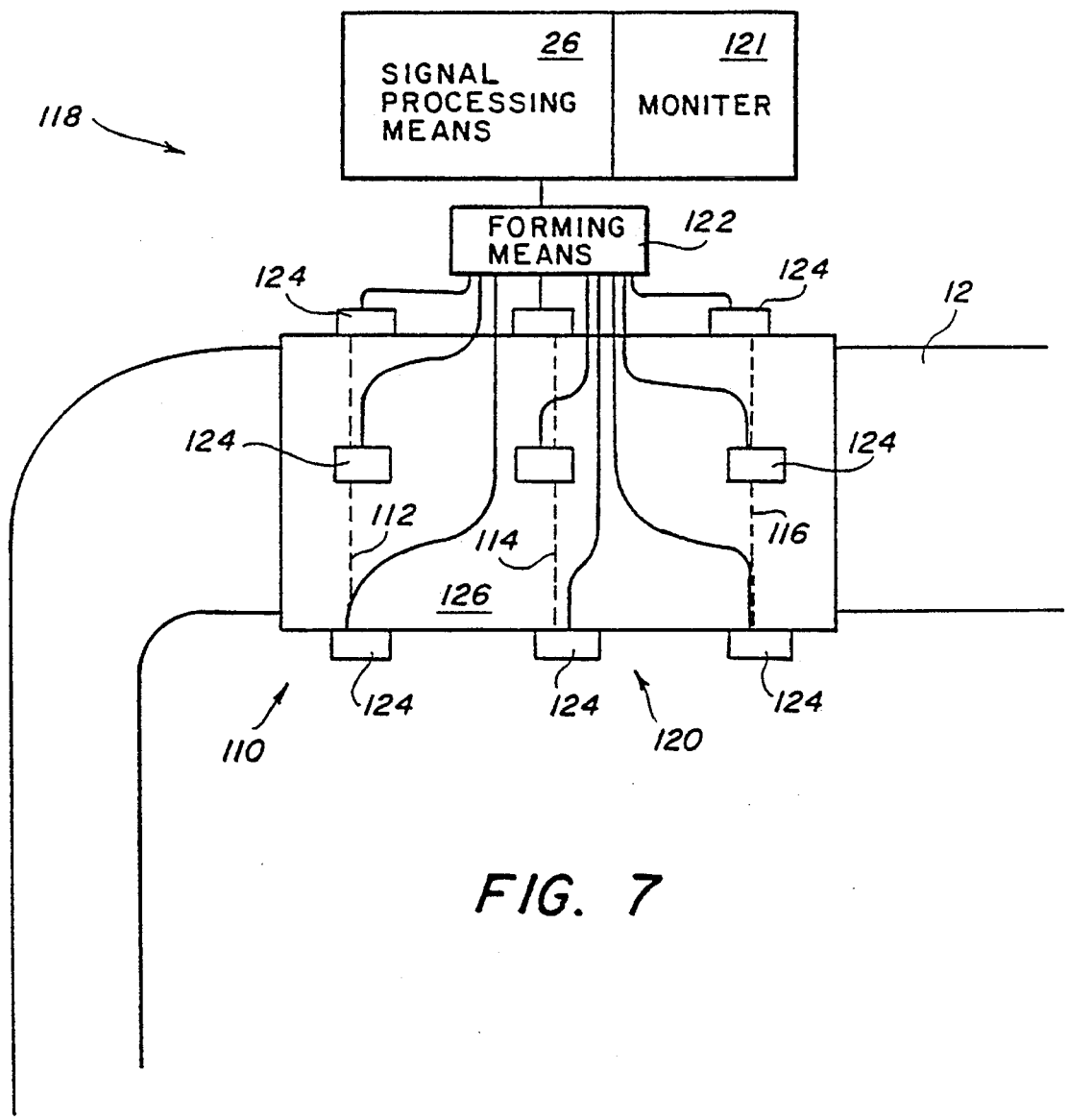
FIG. 7 is a schematic representation showing an apparatus for determining the axial transverse velocity profile.

The present invention also pertains to a method for creating a velocity profile of fluid flowing through an axial length 110 of pipe 12 as shown in FIG. 7. The method comprises the steps of (a) measuring transverse velocity flow of the fluid at a first axial location 112 of the pipe 12 with energy introduced therein. Then, there is the step of (b) measuring transverse velocity flow of the fluid at a second axial location 114 of the pipe 12 with energy introduced therein. Preferably, after step (b), there is the step (c) of forming a profile of the transverse velocity of fluid flowing in the pipe 12 over the axial length 110 of the pipe from the transverse velocity measured at the first axial location 112 and second axial location 114. Preferably, before step (c), there is the step (d) of measuring the transverse velocity of fluid flowing in the pipe 12 at a plurality of additional different axial locations, such as axial location 116 with energy introduced to the pipe 12. After the step (d), there can be the step (e) of fixing a flow meter in contact with the pipe 12 at a desired axial location based on the transverse velocity flow thereat.

Also as shown in FIG. 7, there is an apparatus 118 for creating a velocity profile of fluid flowing through a pipe 12. The apparatus 118 is comprised of means 120 for obtaining transverse velocity flow information of fluid along an axial length 110 of the pipe 12 with energy introduced therein. The apparatus 118 is also comprised of means 122 for forming a transverse velocity profile along the axial length 110 of the pipe 12 from the transverse flow information. The forming means 122 is in communication with the obtaining means 120. Preferably, the obtaining means 120 can be a plurality of transducers 124 disposed in a removable housing, for instance, connected with velcro. The transducers 124 are disposed in the housing 126 such that each transducer 124 has a mate transducer 124, which together form a diametrical path. Individual sets of transducers provide their diametrical path information to the obtaining means 122, which is preferably signal processing means 26 as described above, to calculate the transverse flow. The forming means 122 can also include a monitor 121 which is connected to signal processing means 26 that displays the velocity profile along the axial length 110. A flow meter, for instance, comprised of first transducer 14, second transducer 16, third transducer 20 and fourth transducer 22, as shown in FIG. 1, can then be fixedly attached to the pipe 12 at a location where there is minimal transverse velocity flow so that an accurate a reading as possible of the axial flow through the pipe 12 can be obtained.

The present invention is also an apparatus for measuring the temperature of a flowing fluid 11 in a pipe 12. The apparatus is comprised of means for actively testing the flowing fluid with energy and producing a test signal corresponding to the temperature of the fluid 11. The testing means is in contact with and preferably disposed on the outside of the pipe 12. The apparatus is also comprised of signal processing means 26 for determining the temperature of the fluid 11 based on the test signal.

Preferably, the testing means comprises a first transducer 14 for transmitting ultrasonic signals through the fluid 11 and a second transducer 16 for receiving ultrasonic signals transmitted by the first transducer 14. The second transducer 16 is disposed in an opposing relation with the first transducer 14 such that the ultrasonic signals transmitted by the first transducer 14 travel on a diametric path 18 with respect to the pipe 12 to the second transducer 16. Preferably, the testing means also includes means for measuring pressure of the fluid in the pipe 12, such as a pressure gauge or sensor. The pressure measuring means is in communication with the signal processing means 26 and the pipe 12. The signal processing means 53 preferably determines the temperature of the fluid in the pipe 12 based on the transmission speed of ultrasonic signals transmitted between the first and second transducers and the pressure of the fluid. Preferably, the signal processing means 26 identifies the average temperature of the fluid across the pipe 12 corresponding to the diametric path 18 between the first transducer 14 and second transducer 16. Preferably, to calculate the temperature, Equations 9–14 below can be used in the signal processing means 20, such as a computer. By being disposed on the outside of the pipe 12, the first and second transducers do not interfere with the flow of fluid 11 with the pipe. The temperature of the fluid 11 flowing in the pipe 12 can thus be determined without the apparatus penetrating the envelope defined by the inside diameter, ID, of the pipe 12.

The present invention is also an apparatus for measuring the speed of sound in a fluid 11 flowing in a pipe 12. The apparatus comprises means for testing the flowing fluid 11 and producing a test signal corresponding to the speed of sound of the fluid in the pipe. The testing means is in contact with and preferably disposed on the outside of the pipe 12. The apparatus also includes signal processing means 26 for determining the speed of sound of the fluid in the pipe based on the test signal. Preferably, the testing means is disposed in a gaseous environment on the outside of the pipe 12. Preferably, the testing means comprises a first transducer 14 for transmitting ultrasonic signals through the fluid 11 and a second transducer 16 for receiving ultrasonic signals transmitted by the first transducer 14. The second transducer 16 is disposed in an opposing relation with the first transducer 14 such that the ultrasonic signals transmitted by the first transducer 14 travel on a diametric path 18 with respect to the pipe 12 to the second transducer 16. The speed of sound can be determined by the signal processing means 26, such as a computer, with Equations (5), (7) and (8) and the necessary measured data.

The present invention also pertains to an apparatus 10 for characterizing fluid properties in a pipe 12. The apparatus 10 comprises first means for measuring sound velocity in the fluid and producing a first signal corresponding to the sound velocity. The first measuring means is in communication with the fluid. The apparatus 10 is also comprised of second means for measuring at least one state variable of the fluid and providing a second signal corresponding to the state variable measured. The second means is in communication with the fluid in the pipe. Additionally, the apparatus is comprised of signal processing means 26 in communication with the first and second measuring means for determining fluid properties. As shown in FIG. 1, the second measuring means preferably includes means for measuring pressure of the fluid. The pressure measuring means is connected with the signal processing means 26. The pressure measuring means can be a pressure sensor in communication with the fluid. The first means can include a first transducer 14 and a second transducer 16 in contact with the pipe such that first transducer 14 transmits acoustic energy in a diametric path 24 to the second transducer 16. Each transducer is in communication with the signal processing means 26.

In this embodiment, preferably, the signal processing means 26 also determines specific volume of the fluid. The specific volume can be determined from the "REM calculation" as specific volume cubic feet/pound" in Appendix A. For this calculation, the pressure is independently measured with a pressure gauge and the temperature is calculated from the speed of sound, as described above. Additionally, the signal processing means 24 can determine Reynolds number for the fluid in the pipe from the specific volume and viscosity and consequently PF. It does this in the following way. The determination of the kinematic viscosity (kvis), the profile factor PF and the Reynolds number can be obtained from "REM calculation of meter factor" in Appendix A, where L represents log. The profile correction factor, PF, relates to axial velocity averaged along the acoustic path between the diagonal transducers, $\bar{v}$, with the axial velocity average across the cross sectional area of the flow, $\bar{\bar{v}}$. This is expressed as:

$$\frac{\bar{v}}{\bar{\bar{v}}} = PF$$

The PF will vary depending on three factors. These are:
(1) Average fluid velocity, $\bar{v}$.
(2) Fluid density and viscosity, $\rho$ and $\mu$, respectively.
(3) Cross section dimensions (i.e. ID).

The Reynolds number combines the hydraulic effect of the above 3 factors into one number. The Reynolds number, Re, can be used to determine an expression for the velocity profile (Nikuradse, J. "Laws of Turbulent Flow in Smooth Pipes," NASA TT F-10, 359, October, 1966; Reichardt, H., "Vollständige Darstellung der turbelenten Geskhwindigkeitsverteilung in glatten Leitungen" ZAMM 31, 208–219 (1951), incorporated by reference) and thus the PF may be determined from knowledge of the Reynolds number.

The LEFM first calculates the kinematic viscosity using the curve fit of the published values for water vs. temperature.
where:

$\upsilon$=Kinematic viscosity=$\mu/\upsilon$=absolute viscosity/density
Then, the Reynolds number is calculated:
Re=Reynolds number=$D\bar{\bar{v}}/\upsilon$ The PF is then calculated using published data (i.e. Reichardt and Nikuradse) that express the velocity profile as a function of Reynolds number.

In the apparatus 10, with temperature measuring means, the signal processing means 24 preferably identifies when a boundary between fluid of a first material and fluid of a second material passes through the pipe at the diametrical path. The temperature measuring means can be, for instance, a thermal couple in contact with the pipe 12 or the fluid. Since there is independent identification of temperature and pressure, and with an essentially constant temperature and pressure, a change in specific volume determined by the first and second transducers and signal processing means 26 indicates a change in material in the pipe 12. Knowledge of the pressure, temperature and sound velocity can be used to distinguish fluids which have sound velocities distinct from each other. Typically, fluid with sound velocities that differ by 0.5% at a given temperature and pressure are easily distinguished. Likewise, with knowledge of the pressure and calculated temperature, the specific heat content of water and water density can be determined from a curve fit of published data vs. temperature and pressure. Fluid enthalpy can be determined using the fluid density and specific heat content.

Figure 8:
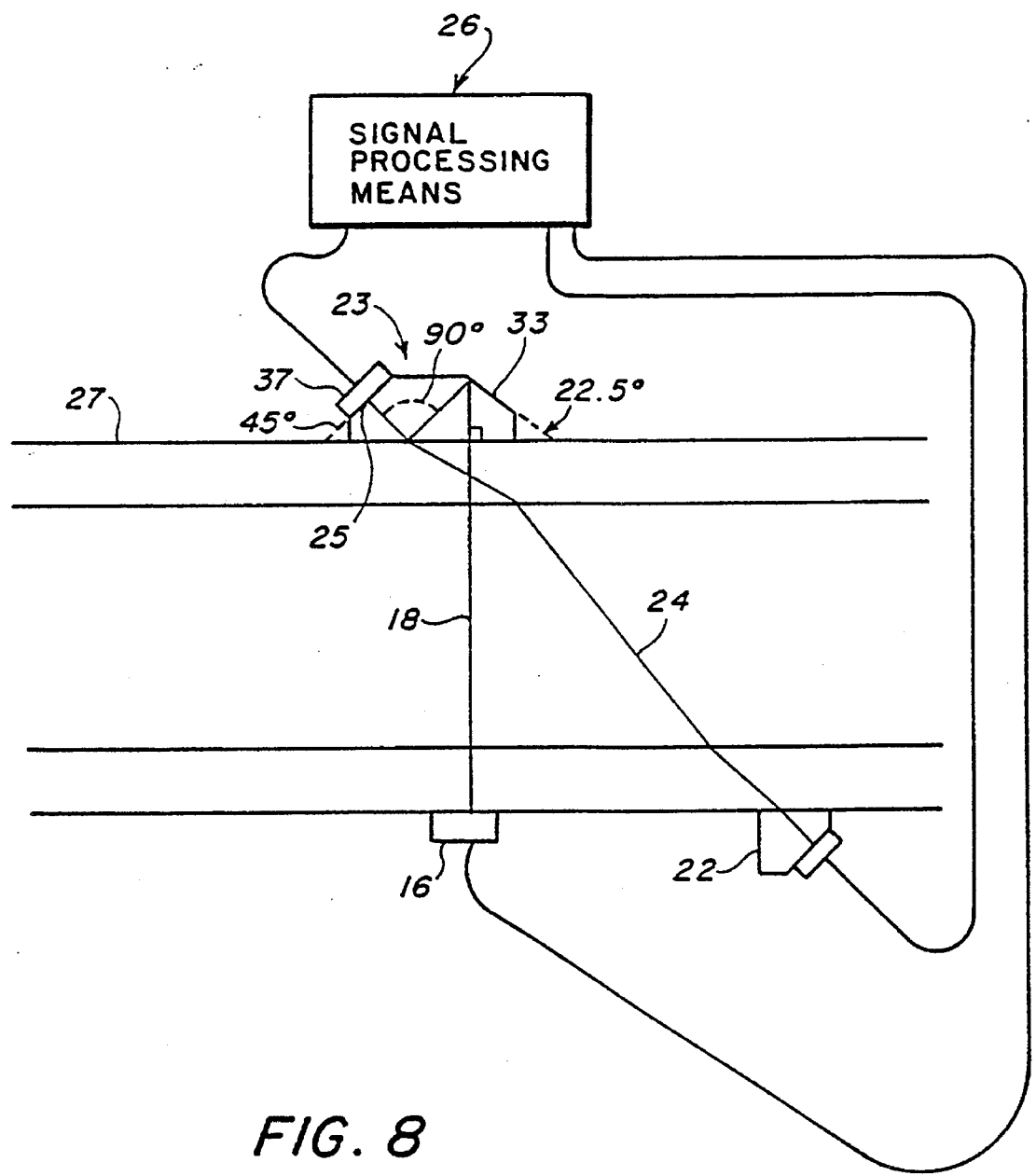
FIG. 8 is a schematic representation of an apparatus for determining fluid flow in a pipe using three transducers.

Another embodiment requires only three transducers to form a diagonal and a diametrical path, as shown in FIG. 8. Second transducer 16 and fourth transducer 22 are the same as described above. In place of first transducer 14 and third transducer 20 is double transducer 23. On a first face 25 forming a 45° angle with the surface 27 is disposed piezoelectric 37 which emits ultrasonic energy. The ultrasonic energy is incident upon the double transducer 23-pipe 12 interface where a portion of the energy is refracted therethrough ultimately to third transducer 22, and a portion of the energy is reflected to free face 33. Free face 33 forms a 22.5° angle with the outer surface 27 of the pipe 12. The reflected energy from the double transducer 23-pipe 12 interface is again reflected by free face 33 such that it forms a right angle with the outer surface of the pipe 12 and is transmitted therethrough to second transducer 16.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

---

: REM High Temperature Strapon Flowmeter method 1
pi = 3.141593     'value of Pi
rad = 180 / pi    'conversion from radians to degrees
REM measured pipe and wedge dimensions
    awc = .247' wedge height cross path, inches
    aw = .7825' wedge height diagonal wedge , inches
    Thetawo = 30.55 / rad
    OD = 16.04' Pipe diameter inches
    ap = .992 'Pipe wall thickness, inches
ID = OD − 2 * ap' calculation of pipe inside diameter -continued

```
    tauEc = (2.64 + 1.075) * .000001'Tau electronics + Tau transducer + Tau cab
cross path, seconds
    tauEd = (1.64 + 1.075) * .000001'Tau electronics + Tau transducer + Tau cab
diagonal path, seconds
        pressg = 1100' measured fluid pressure
        press = pressg + 14.7'conversion from press gauge to press absolute
REM measured values of times
    td = .0003387' average transit time diagonal path, seconds
    tc = .00029542#' average transit time cross path, seconds
    dtd = 7.59E-07'difference in transit time diagonal path, seconds
    dtc = -1E-09'difference in transit time cross path, seconds
REM Coefficients used in calculation of velocity of sound in pipe and wedge
    Acw = 98299: bcw = -.000396054#: ccw = -2.08E-07'KKB Vespal corrected ??
    Acpt = 127700: Bcpt = -.0000925
    Acpl = 235600: Bcpl = -.0000735
REM coefficients for calculation of lkvis= natural log kvis
    Akv = -5.507787: Bkv = -.01557479#: Ckv = 2.87701E-05: Dkv = -1.8516E-08
REM calculation of fluid temperature
    Th = 660: Tl = 165: 'temperature limits
    dto = .001 ' max error in calculation of temp
    dt = Th - Tl
DO
    i = i + 1
    dt = dt / 2
    temp = Tl + dt
    cwc = Acw * (1 + bcw * tempwc + ccw * tempwc ^ 2)    ' velocity in wedge, inches
/sec
    cpl = Acpl * (1 + Bcpl * tempp)'longitudinal velocity in steel, inches/sec
    tr = temp - 175.1
    vt = 5290.52 - .15302 * tr - .0138265 * tr ^ 2 + 3.326E-06 * tr ^ 3 + 3.11042
-08 * tr ^4 - 5.1131E-11 * tr ^ 5
    dvdp = 756.78 (725 - temp) + 6.3846 - .034241 * (725 - temp) + 7.407E-05 * (
725 - temp) ^ 2 - 5.666E-08 * (725 - temp) ^ 3
    vtp = vt - (4437 - press) * dvdp * .02253
    cf = vtp * 12
    tau1 = tauEc + 2 * awc / cwc + 2 * ap / cpl'Tau for cross path
    F1 = tc - tau1 - ID / cf
    IF F1 >= 0 THEN Tl = temp
LOOP UNTIL ABS(dt) < dto OR F1 = 0
REM calculation of Tangent phif
    sphiw = SIN(Thetawo)' Sine of wedge angle
    cw = Acw * (1 + bcw * temp + ccw * temp ^ 2) ' velocity of sound in wedge,i
s/sec
    sphif = cf * sphiw / cw' Sine of angle on fluid
    cphif = SQR(1 - sphif ^ 2)' Cosine of angle in fluid
    tphif = sphif / cphif' Tangent of angle in fluid
REM calculation of meter factor
    v = cf ^ 2 / 2 / ID / tphif * (dtd - dtc)
    Lkvis = Akv + Bkv * temp + Ckv * temp ^ 2 + Dkv * temp ^ 3 'natural log kine
tic viscosity of water, square inches/sec
    lre = LOG(ABS(v * ID)) - Lkvis 'Calculation of natural log Reynold's number
    PF = 1.0144 - .8442 / lre    'meter factor
REM calculation of flow
Q = pi * ID * PF * cf ^ 2 / (8 * tphif) * (dtd - dtc)' flow in cubic inches/sec
PRINT Q
END
    REM calculation os specific volume cubic feet/pound
        svt = .01566 + 6.97E-06 * temp - 6.27E-08 * temp ^ 2 + 3.61E-10 * temp ^ 3 - 7.34E-13 * temp ^ 4 +0 5.5E-16 * temp ^5
        dsvdp = 70931 / (700 - temp) - 17.9 + .01621 * (700 - temp) + .000004 * (700 - temp) ^ 2
        svtp = svt + (3000 - press) * dsvdp * 1E-08
```

What is claimed is:

1. An apparatus for determining fluid flow rate in a pipe comprising:

a first transducer for transmitting acoustic energy, said first transducer in acoustic contact with said pipe;

a second transducer for receiving said acoustic energy from said first transducer, said second transducer in contact with said pipe such that the acoustic energy transmitted by the first transducer follows a substantially diametrical path through the fluid in the pipe;

a third transducer for transmitting acoustic energy, said third transducer in acoustic contact with said pipe;

a fourth transducer for receiving said acoustic energy transmitted from said third transducer, said fourth transducer in acoustic contact with said pipe such that the acoustic energy transmitted by said third transducer follows a diagonal path through the fluid in the pipe, said diametrical path adjacent to said diagonal path;

wherein each transducer is disposed on the outside of the pipe and acoustic energy follows a path through the pipe wall, and signal processing means for determining the flow rate of fluid in the pipe based on acoustic energy received by the second and fourth transducers with the energy received by the second transducer used to determine the speed of sound of the fluid so the flow of fluid can be determined, said second and fourth transducers in communication with said signal processing means.

2. An apparatus as described in claim 1 wherein the third transducer and fourth transducer are located at upstream and downstream positions relative to one another, said third and fourth transducers adapted to alternatively function as transmitter and receiver so as to cause acoustic signals to travel through the fluid alternatively in upstream and downstream directions along a diagonal path between the third transducer and the fourth transducer; and wherein the first and second transducers are adapted to alternatively function as transmitter and receiver so as to cause acoustic signals to travel through the fluid alternatively between said first and second transducers along a diametrical path, said diametrical path adjacent to said diagonal path; and wherein the signal processing means includes means for determining the flow rate of fluid in the pipe based on the transmission speed of acoustic signals transmitted between the first and second transducers and the third and fourth transducers, respectively.

3. An apparatus as described in claim 2 wherein the pipe has an outside surface and the first, second, third, fourth transducers are fixed to the outside surface of the pipe.

4. An apparatus as described in claim 3 including a plurality of sets of transducers for alternately transmitting and receiving acoustic signals through the fluid along a plurality of diagonal paths.

5. An apparatus as described in claim 4 including a plurality of sets of transducers for alternately transmitting and receiving acoustic energy through the fluid along a plurality of diametrical paths.

6. An apparatus as described in claim 1 wherein the third transducer and the fourth transducer are aligned with each other such that acoustic energy transmitted by the third transducer follows a diagonal path to the fourth transducer which is formed by reflection of the acoustic energy off of the pipe.

7. An apparatus as described in claim 1 wherein the pipe has an outside surface and an interior and the third and fourth transducers are disposed in the pipe beneath the outside surface such that acoustic energy transmitted by the third transducer is introduced directly into the interior of the pipe, and acoustic energy is received by the fourth transducer directly from the interior of the pipe.

8. An apparatus for determining fluid flow rate in a pipe comprising:

means for providing acoustic energy on a diagonal path through the fluid, said diagonal providing means fixedly disposed on said pipe;

means for receiving said acoustic energy on the diagonal path, said diagonal receiving means disposed on said pipe;

means for providing acoustic energy on a diametrical path through the fluid, said diametrical providing means disposed on said pipe;

means for receiving said acoustic energy on the diametrical path, said diametrical receiving means disposed on said pipe;

wherein each providing means and receiving means is disposed on the outside of the pipe and acoustic energy follows a path through the pipe wall, and means for determining the flow rate of fluid in the pipe based on the acoustic energy received by the diagonal receiving means and the acoustic energy received by the diametrical receiving means with the energy received by the diametrical receiving means used to determine the speed of sound of the fluid so the flow rate of fluid can be determined, said determining means in communication with the diagonal providing means and the diagonal receiving means, and the diametric providing means and the diametric receiving means.

9. An apparatus as described in claim 8 wherein the diagonal providing means and diagonal receiving means comprises a third transducer and a fourth transducer, respectively, located on the pipe at upstream and downstream positions relative to one another and the diametric providing means and diametric receiving means comprises a first transducer and a second transducer, respectively, located on the pipe at opposed diametric positions relative to one another.

10. An apparatus as described in claim 9 wherein said third and fourth transducers adapted to alternatively function as transmitter and receiver so as to cause acoustic signals to travel through the fluid alternatively in upstream and downstream directions along the diagonal path between the third and fourth transducers and said first and second transducers adapted to alternatively function as transmitter and receiver so as to cause acoustic signals to travel through the fluid alternatively along the diametrical path between said first and second transducers.

11. An apparatus as described in claim 10 wherein the means for determining flow rate includes signal processing means.

12. An apparatus as described in claim 11 wherein the signal processing means includes means for determining the flow rate of fluid in the pipe based on the transmission speed of acoustic signals transmitted between the first and second transducers and the third and fourth transducers, respectively.

13. An apparatus as described in claim 12 including a plurality of sets of transducers for alternately transmitting and receiving acoustic signals through the fluid along a plurality of diagonal paths.

14. An apparatus as described in claim 13 including a plurality of sets of transducers for alternately transmitting and receiving acoustic energy through the fluid along a plurality of diametrical paths.

15. An apparatus for determining fluid flow rate in a pipe comprising:

means for providing acoustic energy on a diagonal path through the fluid, said diagonal providing means in contact with said pipe;

means for providing acoustic energy on a diametrical path through the fluid, said diametrical providing means in contact with said pipe;

means for receiving said acoustic energy on the diagonal path;

means for receiving said acoustic energy on the diametrical path;

wherein each said providing mean and each said receiving means is disposed on the outside of the pipe and acoustic energy follows a path through the pipe wall to said providing and said receiving means, and means for determining the flow rate of fluid in the pipe based on the acoustic energy of the diagonal providing means and the acoustic energy of the diametrical providing means, said determining means in communication with the diagonal providing means and the diametric providing means.

16. An apparatus as described in claim 15 wherein the diagonal providing means comprises a third transducer and a fourth transducer located on the pipe at upstream and downstream positions relative to one another and first and second transducers located on the pipe at opposed diametric positions relative to one another.

17. An apparatus as described in claim 16 wherein said third and fourth transducers adapted to alternatively function as transmitter and receiver so as to cause acoustic signals to travel through the fluid alternatively in upstream and downstream directions along the diagonal path between the third and fourth transducers and said first and second transducers adapted to alternatively function as transmitter and receiver so as to cause acoustic signals to travel through the fluid alternatively along the diametrical path between said first and second transducers.

18. An apparatus as described in claim 17 wherein the means for determining flow rate includes signal processing means.

19. An apparatus as described in claim 18 wherein the signal processing means includes means for determining the flow rate of fluid in the pipe based on travel time of acoustic signals transmitted between the first and second transducers, and the third and fourth transducers, respectively.

20. An apparatus for determining fluid flow in a pipe comprising:

- a first transducer for transmitting acoustic energy, said first transducer in acoustic contact with said pipe;
- a second transducer for receiving said acoustic energy from said first transducer, said second transducer in contact with said pipe such that the acoustic energy transmitted by the first transducer follows a substantially diametrical path through the fluid in the pipe;
- wherein each transducer is disposed on the outside of the pipe and acoustic energy follows a path through the pipe wall, and
- a third transducer for transmitting acoustic energy, said third transducer in acoustic contact with said pipe;
- a fourth transducer for receiving said acoustic energy transmitted from said third transducer, said fourth transducer in acoustic contact with said pipe such that the acoustic energy transmitted by said third transducer follows a diagonal path through the fluid in the pipe, said diametrical path adjacent to said diagonal path, wherein the third transducer and fourth transducer are located at upstream and downstream positions relative to one another, said third and fourth transducers are adapted to alternatively function as transmitter and receiver so as to cause acoustic signals to travel through the fluid alternatively in upstream and downstream directions along a diagonal path between the third transducer and the fourth transducer; and wherein the first and second transducers are adapted to alternatively function as transmitter and receiver so as to cause acoustic signals to travel through the fluid alternatively between said first and second transducers along the diametrical path, said diametrical path adjacent to said diagonal path; and
- signal processing means for determining the flow of fluid in the pipe based on acoustic energy received by the second and fourth transducers, said second and fourth transducers in communication with said signal processing means wherein the signal processing means includes means for determining the flow rate of fluid in the pipe based on how long it takes of acoustic signals transmitted between the first and second transducers and the third and fourth transducers, respectively.

21. An apparatus for determining fluid flow in a pipe comprising:

- means for providing acoustic energy on a diagonal path through the fluid, said diagonal providing means fixedly disposed on said pipe, the diagonal providing means comprises a third transducer and a fourth transducer located on the pipe at upstream and downstream positions relative to one another;
- means for providing acoustic energy on a diametrical path through the fluid, said diametrical providing means disposed on said pipe, the diametrical providing means comprises a first transducer and a second transducer located on the pipe at opposed diametric positions relative to one another;
- wherein each said providing means and said receiving means is disposed on the outside of the pipe and acoustic energy follows a path through the pipe wall, and
- means for determining the flow of fluid in the pipe based on the acoustic energy of the diagonal providing means and the acoustic energy of the diametrical providing means, said determining means in communication with the diagonal providing means and the diametric providing means.

* * * * *